United States Patent
Namavari et al.

(10) Patent No.: US 9,402,925 B2
(45) Date of Patent: Aug. 2, 2016

(54) PROBES AND METHODS OF IMAGING A BACTERIAL INFECTION

(71) Applicant: The Board of Trustees of the Leland Stanford Junior University, Palo Alto, CA (US)

(72) Inventors: Mohammad Namavari, Palo Alto, CA (US); Gayatri Gowrishankar, Cupertino, CA (US); Sanjiv S. Gambhir, Portola Valley, CA (US)

(73) Assignee: The Board of Trustees of the Leland Stanford Junio, Palo Alto, CA (US)

( * ) Notice: Subject to any disclaimer, the term of this patent is extended or adjusted under 35 U.S.C. 154(b) by 0 days.

(21) Appl. No.: 14/204,402

(22) Filed: Mar. 11, 2014

(65) Prior Publication Data

US 2014/0314671 A1    Oct. 23, 2014

Related U.S. Application Data

(60) Provisional application No. 61/777,690, filed on Mar. 12, 2013.

(51) Int. Cl.
*A61K 51/04* (2006.01)

(52) U.S. Cl.
CPC .................. *A61K 51/0491* (2013.01)

(58) Field of Classification Search
None
See application file for complete search history.

(56) References Cited

U.S. PATENT DOCUMENTS

| 6,596,546 | B1 | 7/2003 | Jolley et al. |
| 7,196,073 | B2 | 3/2007 | Marciani et al. |
| 2004/0137525 | A1 | 7/2004 | Jolley et al. |
| 2010/0240878 | A1 | 9/2010 | Barbeau et al. |

FOREIGN PATENT DOCUMENTS

WO    2012097223    1/2013

OTHER PUBLICATIONS

Brunkhorst et al. Acarbose, a pseudooligosaccharide, is transported but not metabolized by the maltose-maltodextrin system of *Escherichia coli*. 1999 J. Bacteriol. 181: 2612-2619.*

Ning, X., et al (2011) Maltodextrin-based imaging probes detect bacteria in vivo with high sensitivity and specificity Nat Mater 10(8):602-7.

* cited by examiner

*Primary Examiner* — Michael G Hartley
*Assistant Examiner* — Jennifer Lamberski
(74) *Attorney, Agent, or Firm* — Thomas|Horstemeyer, LLP

(57) ABSTRACT

Embodiments of the present disclosure provide for labeled probes such as labeled maltose probes and labeled acarbose probes, methods of making labeled probes, pharmaceutical compositions including labeled probes, methods of using labeled probes, methods of diagnosing, localizing, monitoring, and/or assessing bacterial infections, using labeled probes, kits for diagnosing, localizing, monitoring, and/or assessing bacterial infections, using labeled probes, and the like.

5 Claims, 8 Drawing Sheets

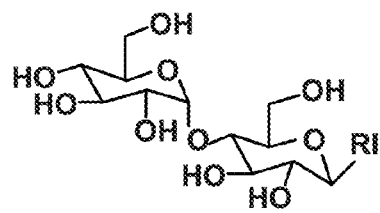
1-RI-maltose
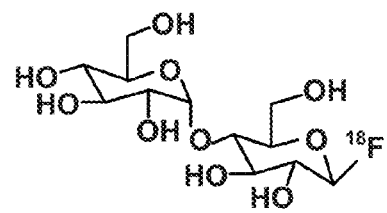
1-$^{18}$F-fluromaltose
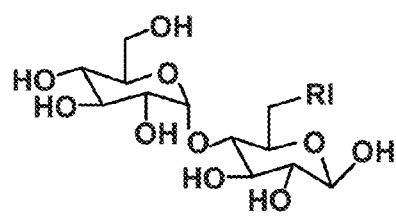
6-RI-maltose
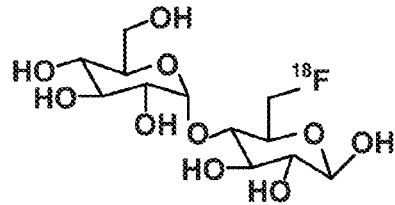
6-$^{18}$F-fluromaltose
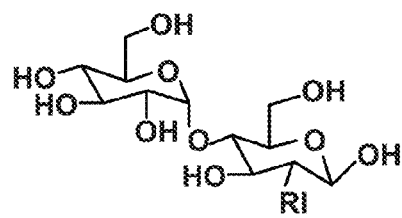
2-RI-maltose
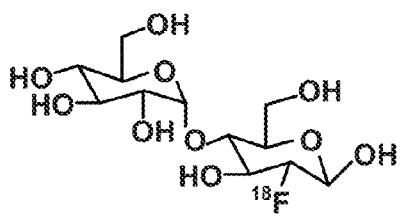
2-$^{18}$F-fluromaltose
FIG. 1.1A

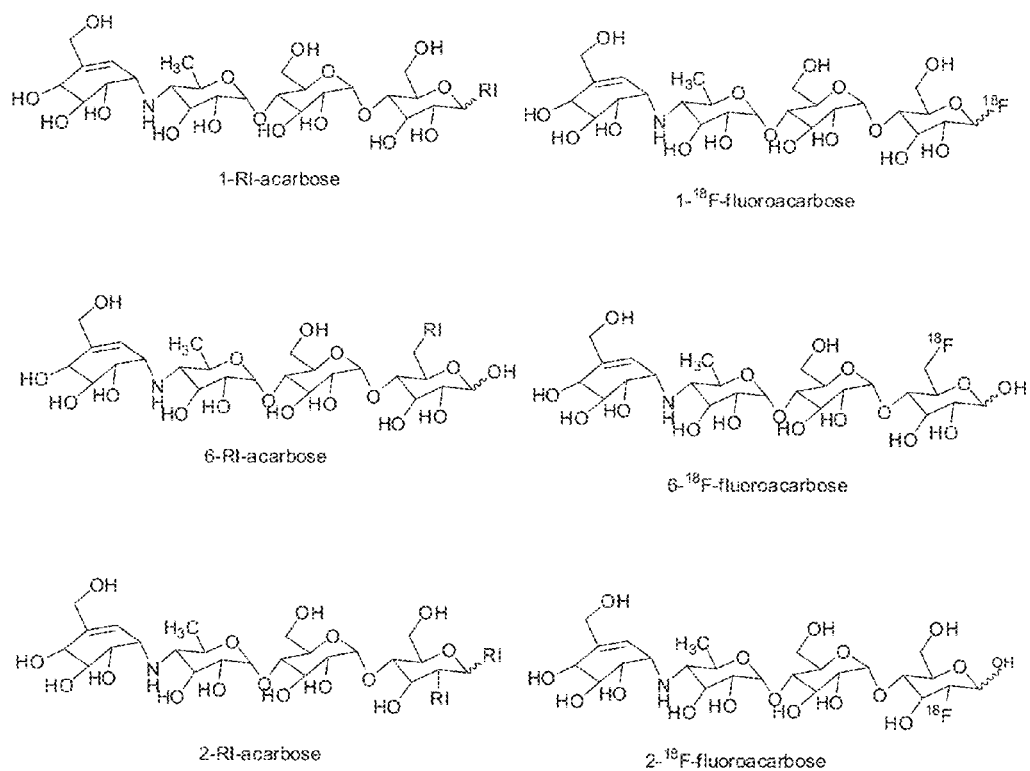
FIG. 1.1B

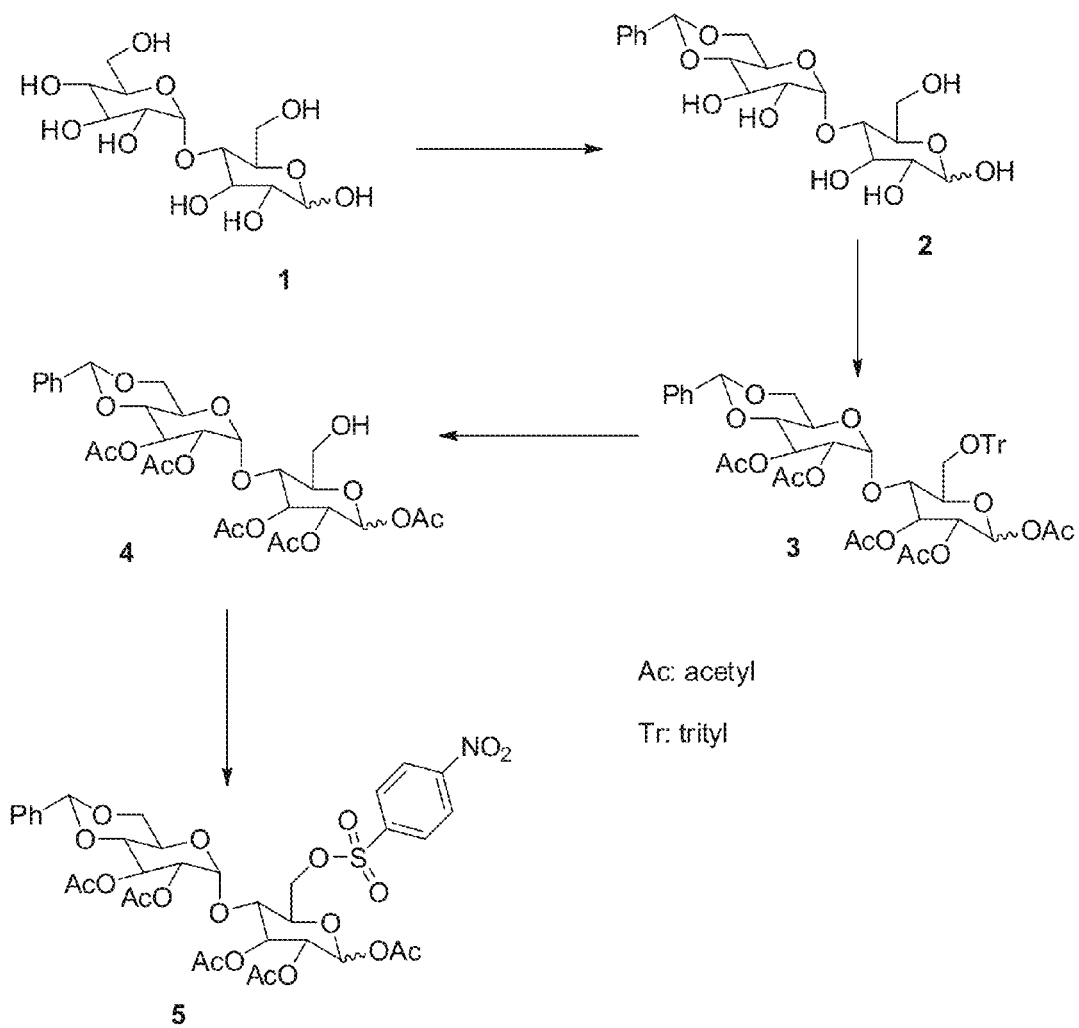
Scheme 1.
FIG. 2.1A

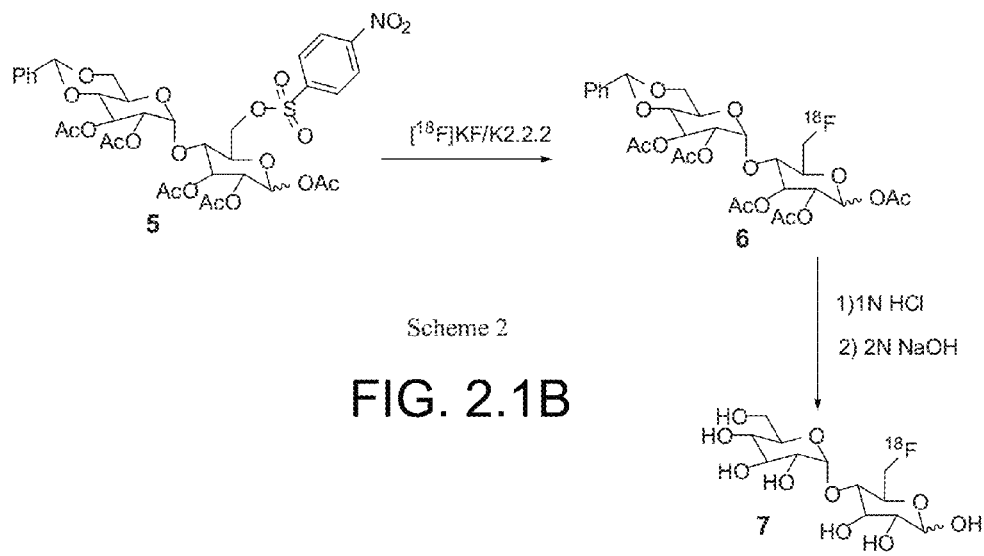
Scheme 2
FIG. 2.1B
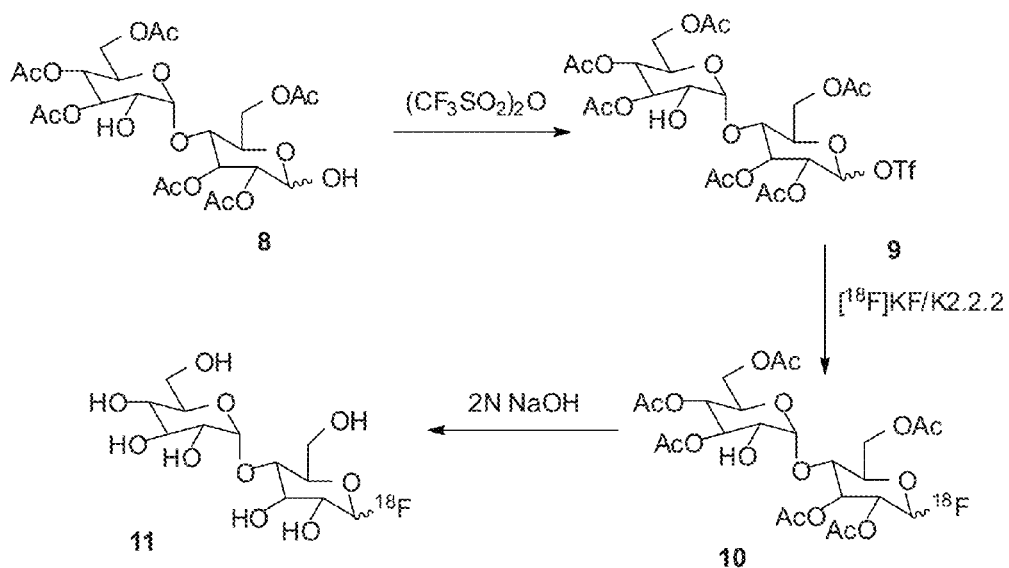
Ac: acetyl   Tf: trifyl   Scheme 3
FIG. 2.1C

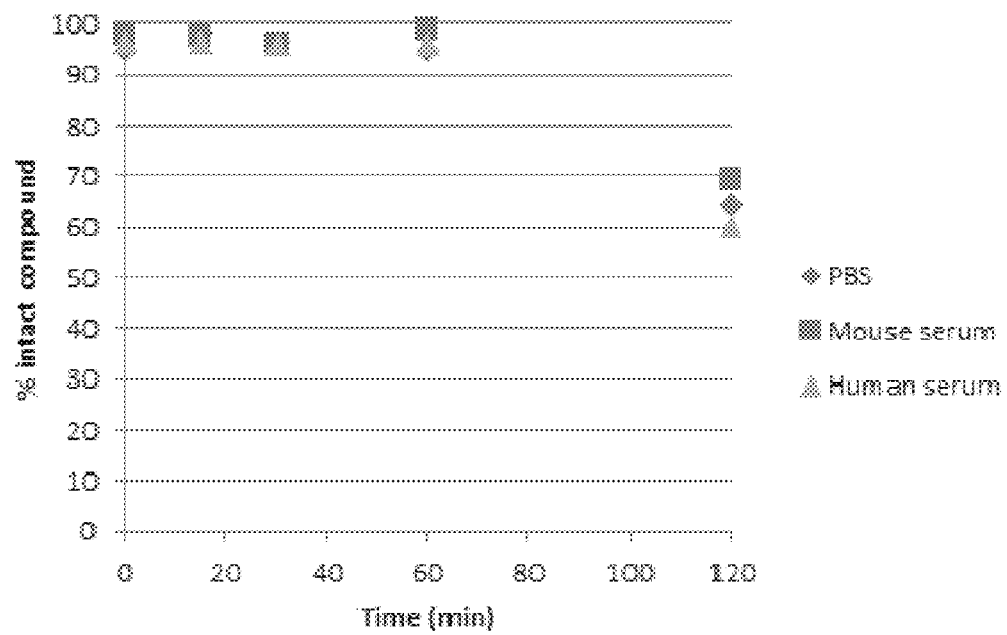
FIG. 2.2
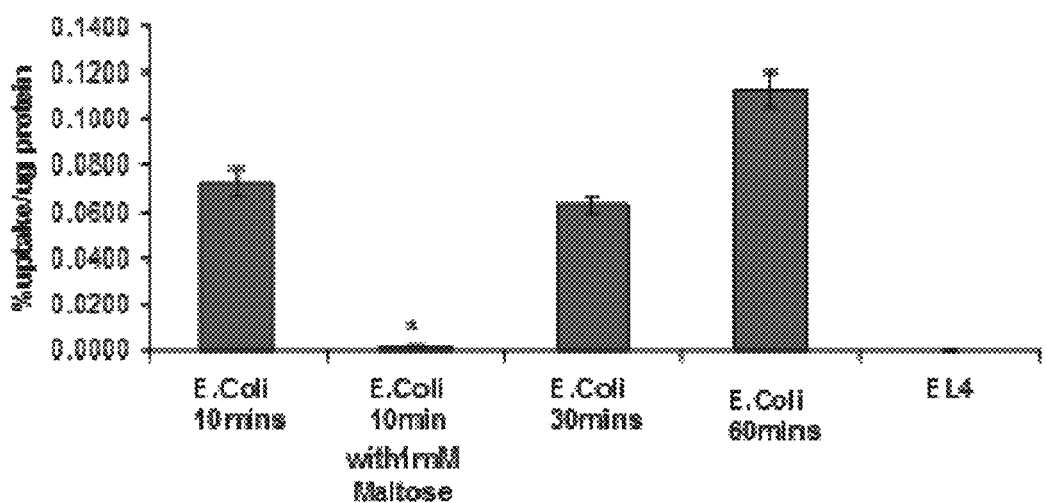
FIG. 2.3

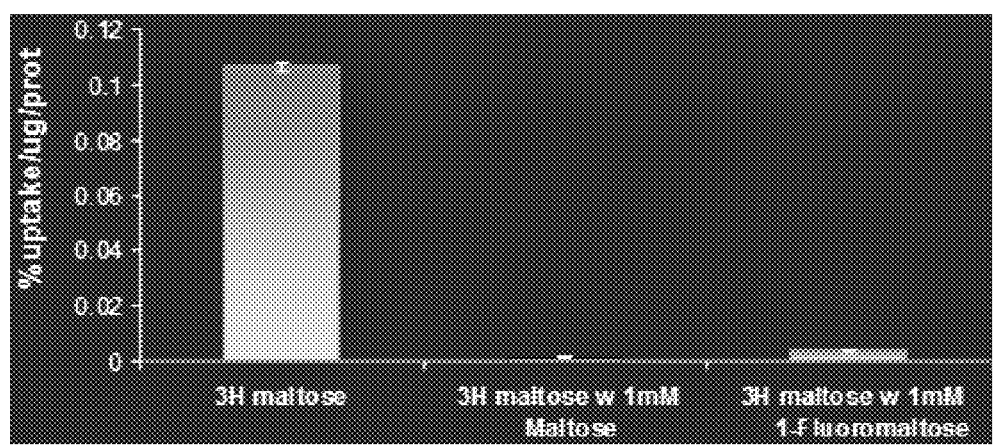
FIG. 2.4

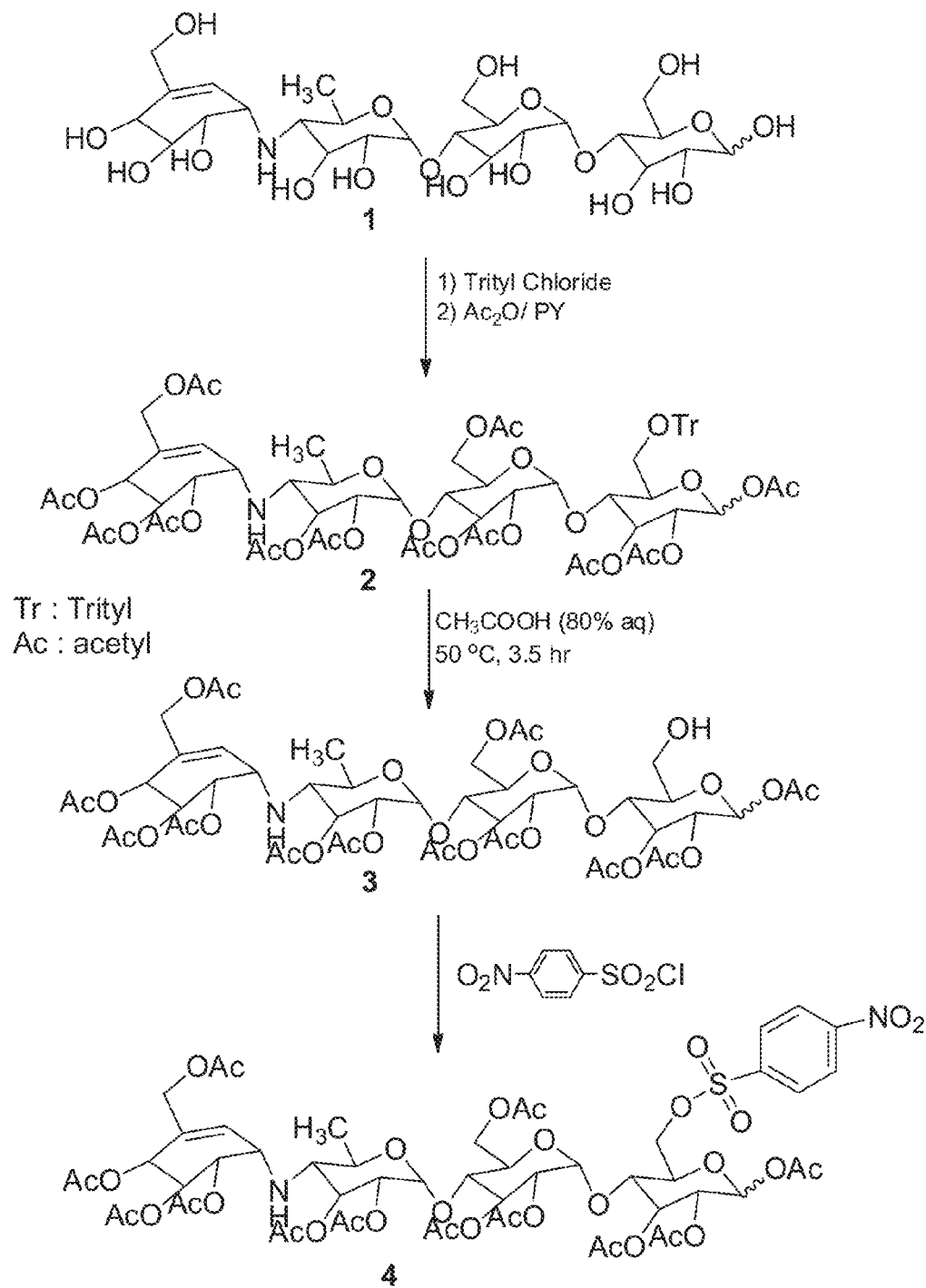
Scheme 1, Synthesis of 6-nosyl-peracetylacarbose
FIG. 3.1

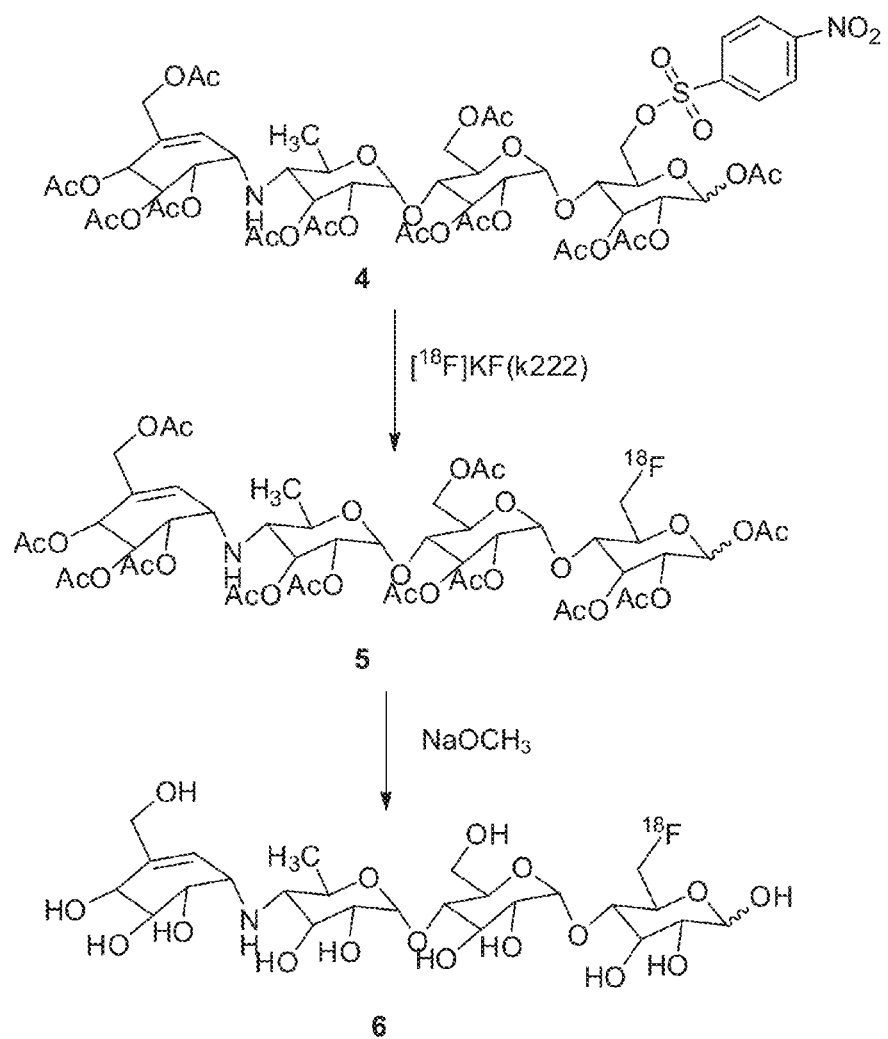
Scheme 2, Synthesis of [18F]Fluoroacarbose
FIG. 3.2

PROBES AND METHODS OF IMAGING A BACTERIAL INFECTION

CLAIM OF PRIORITY TO RELATED APPLICATION

This application claims priority to U.S. provisional application entitled "PROBES AND METHODS OF IMAGING A BACTERIAL INFECTION" having Ser. No. 61/777,690, filed on Mar. 12, 2013, which is entirely incorporated herein by reference.

BACKGROUND

Gram negative and gram-positive bacteria are the most common causes of infection. Early detection of bacterial infection is correlated with greater prognosis for full recovery. Conventional anatomic imaging techniques such as magnetic resonance imaging (MRI) and computed tomography (CT) are incapable of reliably distinguishing infection from sterile inflammation. Thus, there is a need to overcome these deficiencies.

SUMMARY

Embodiments of the present disclosure provide for labeled probes such as labeled maltose probes and labeled acarbose probes, methods of making labeled probes, pharmaceutical compositions including labeled probes, methods of using labeled probes, methods of diagnosing, localizing, monitoring, and/or assessing bacterial infections, using labeled probes, kits for diagnosing, localizing, monitoring, and/or assessing bacterial infections, using labeled probes, and the like.

In an embodiment, the method includes imaging a bacterial infection in a subject, where the method includes: administering to the subject a labeled probe selected from a labeled maltose probe and a labeled acarbose probe; imaging at least a portion of the subject; and detecting the labeled probe, wherein the location of the labeled probe corresponds to bacterial infection.

In an embodiment, the method of screening for an agent for treating a bacterial infection in a sample or subject, where the method includes: contacting the sample with a labeled probe selected from a labeled maltose probe and a labeled acarbose probe, wherein a bacterial infection is present in the sample; contacting an agent with the sample; imaging at least a portion of the sample; and detecting the labeled probe, wherein the location of the labeled probe corresponds to the bacterial infection, wherein the size of the location is monitored over time.

In an embodiment, the composition includes: a labeled probe, wherein the labeled probe includes: 1-RI-maltose probe, 2-RI-maltose probe, 6-RI-maltose probe, 1-RI-acarbose probe, 2-RI-acarbose probe and 6-RI-acarbose probe, where RI is a radiolabel.

In an embodiment, the method of making 6-[$^{18}$F]-fluoromaltose can be described by the following reaction scheme:

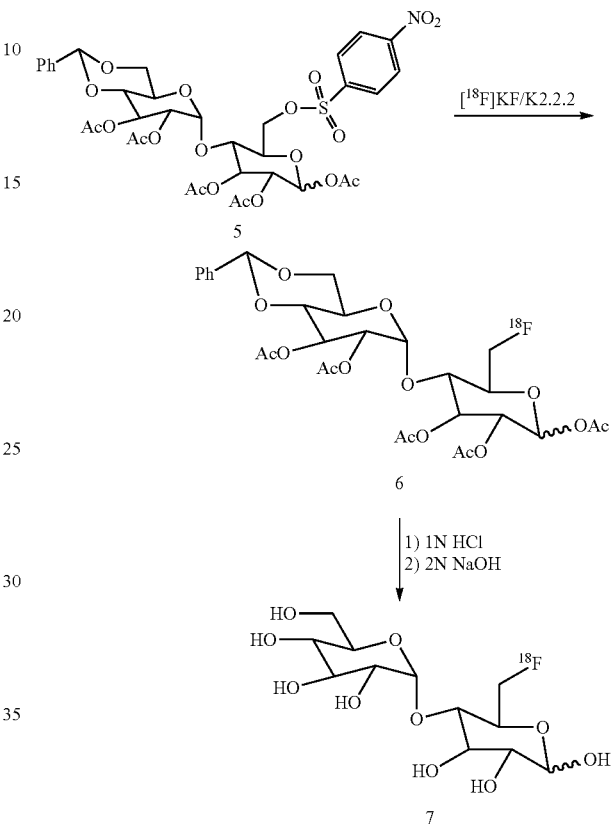

wherein the synthesis utilizes the reaction between the leaving group nosylate in (5) and anhydrous [$^{18}$F]KF/Kryptofix 2.2.2 in acetonitrile to produce 1,2,3-tri-O-acetyl-4-O-(2',3'-di-O-acetyl-4',6'-benzylidene-α-D-glucopyranosyl)-6-deoxy-6-[$^{18}$F]fluoro-D-glucopranoside (6), and wherein acid hydrolysis of (6) followed by its basic hydrolysis produced the final 6-[$^{18}$F]-fluoromaltose (7).

In an embodiment, the method of making 1-[$^{18}$F]-fluoromaltose can be described by the following reaction scheme:

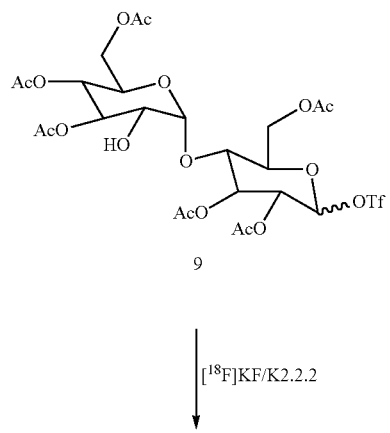

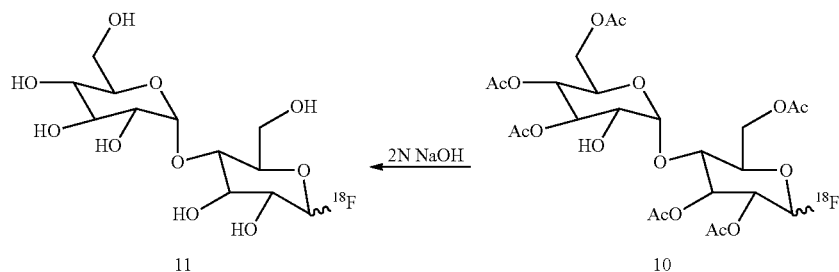

wherein 1-[$^{18}$F]-labeled maltose derivative (10) was prepared by nucleophilic displacement of triflate group in precursor (9) by [$^{18}$F]fluoride ion using anhydrous [$^{18}$F]KF/Kryptofix 2.2.2, wherein (10) is de-protected with basic hydrolysis to afford 4-O-(α-D-glucopyranosyl)-1-deoxy-1-[$^{18}$F]-fluoro-D-glucopyranoside (1-[$^{18}$F]fluoromaltose (11)).

In an embodiment, the method of making 6-[$^{18}$F]-fluoro-acarbose can be described by the following reaction scheme:

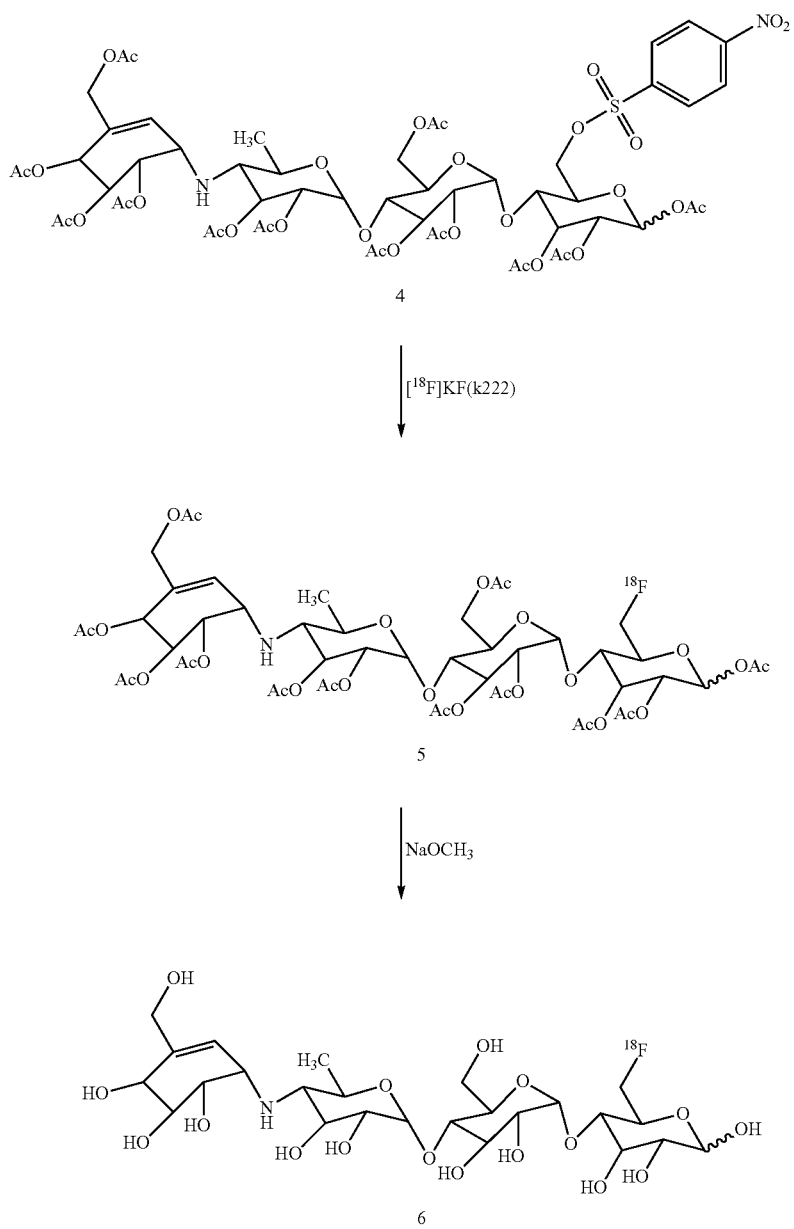

wherein [$^{18}$F]-labeled acarbose derivative (5) was prepared by nucleophilic displacement of nosylate group in (4) by [$^{18}$F]fluoride ion using anhydrous [$^{18}$F]KF/Kryptofix 2.2.2, wherein (5) is de-protected with basic hydrolysis to afford [$^{18}$F]-6-fluoroacarbose (6).

Other compositions, methods, features, and advantages will be, or become, apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1.1A and 1.1B illustrate embodiments of the labeled probes.

FIG. 2.1A illustrates Scheme 1, which shows the synthesis of 1,2,3-tri-O-acetyl-4-O-(2',3'-di-O-acetyl-4',6'-benzylidene-α-D-glucopyranosyl)-6-deoxy-6-O-nosyl-D-glucopranoside (5), the [$^{18}$F]-6-fluoromaltose precursor.

FIG. 2.1B illustrates Scheme 2, which shows the synthesis of 4-O-(α-D-glucopyranosyl)-6-deoxy-6-[$^{18}$F]-fluoro-D-glucopyranoside (6-[$^{18}$F]-fluoromaltose, 7).

FIG. 2.1C illustrates Scheme 3, which shows the synthesis of 4-O-(α-D-glucopyranosyl)-1-deoxy-1-[$^{18}$F]-fluoro-D-glucopyranoside (1-[$^{18}$F]-fluoromaltose, 11).

FIG. 2.2 illustrates the stability of 6-[$^{18}$F]-fluoromaltose 7 in PBS, mouse and human serum at 37° C.

FIG. 2.3 illustrates the uptake of 6-[$^{18}$F]-fluoromaltose in vitro in *Escherichia coli* and a mammalian cell line EL4 at the indicated times. * indicates statistical significance.

FIG. 2.4 illustrates that maltose and 1-fluoromaltose effectively compete with $^3$H-maltose uptake by *Escherichia coli*.

FIG. 3.1 illustrates Scheme 1, which illustrates the synthesis of 6-nosyl-peracetylacarbose.

FIG. 3.2 illustrates Scheme 2, which illustrates the synthesis of [18F] fluoroacarbose.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, molecular imaging, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

By "administration" or "administering" is meant introducing a probe or a labeled probe (also referred to as the "imaging agent") (e.g., [18F]-fluoromaltose probe or [18F]-fluroacarbose) of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the labeled probe of the present disclosure is defined as an amount sufficient to yield an acceptable image using equipment that is available for clinical use. A detectably effective amount of the labeled probe of the present disclosure may be administered in more than one injection. The detectably effective amount of the labeled probe of the present disclosure can vary according to factors such as the degree of susceptibility of the individual, the age, sex, and weight of the individual, idiosyncratic responses of the individual, and the like. Detectably effective amounts of the probe of the present disclosure can also vary according to instrument and film-related factors. Optimization of such factors is well within the level of skill in the art.

As used herein, the term "host" or "subject" includes vertebrates such as humans and mammals (e.g., cats, dogs, horses, etc.). Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living subject" refers to a subject noted above that is alive and is not dead. The term "living subject" refers to the entire subject and not just a part excised (e.g., a liver or other organ) from the living subject.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over the background signal.

The term "detectable signal" is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

The phrase "bacterial infection" can refer to a bacteria colonizing a tissue or organ of a subject, where the colonization causes harm to the subject. The harm can be caused directly by the bacteria and/or by toxins produced by the bacteria. Reference to bacterial infection includes also includes bacterial disease.

Bacteria that cause bacterial infection are called pathogenic bacteria. The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and

*Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides*, and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum*, other *Clostridium* species, *Pseudomonas aeruginosa*, other *Pseudomonas* species, *Campylobacter* species, *Vibrio cholera, Ehrlichia* species, *Actinobacillus pleuropneumoniae, Pasteurella haemolytica, Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi*, other *Hemophilus* species, *Yersinia pestis, Yersinia enterolitica*, other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium*, or any strain or variant thereof. The Gram-positive bacteria may include, but is not limited to, Gram positive Cocci (e.g., *Streptococcus, Staphylococcus*, and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae).

General Discussion

Embodiments of the present disclosure provide for labeled probes such as labeled maltose probes and labeled acarbose probes, methods of making labeled probes, pharmaceutical compositions including labeled probes, methods of using labeled probes, methods of diagnosing, localizing, monitoring, and/or assessing bacterial infections, using labeled probes, kits for diagnosing, localizing, monitoring, and/or assessing bacterial infections, using labeled probes, and the like. In particular, the present disclosure includes methods relating to non-invasive imaging (e.g., using positron emission tomography (PET) imaging system) using labeled maltose probes, such as a 1-$^{18}$F-maltose probe, 2-$^{18}$F-maltose probe, and 6-$^{18}$F-maltose probe, and labeled acarbose probes, such as 1-$^{18}$F-acarbose probe, 2-$^{18}$F-acarbose probe and 6-$^{18}$F-acarbose probe, in vivo. Additional details are described in the Examples.

Embodiments of the present disclosure are advantageous for at least the following reasons. Maltose is used in pathways of multiple types of pathogenic bacteria (e.g., *Escherichia coli, Bacillus subtilis, Streptococcus pneumoniae, Staphylococcus aureus, Pseudomonas aeruginosa, Listeria monocytogenes*). Maltose is taken up at a rate of ten times that of glucose, and maltose is not taken up by mammalian cells. An advantage of using a labeled maltose probe is that it is a specific substrate for bacteria and can be used to image bacterial infections in mammals. Also, maltose transporters are present in most pathogenic bacteria, so labeled maltose probes can be used to image multiple types of infections and/or differentiate between bacterial and viral infections. Similarly, acarbose is a pseudooligosaccharide, which is transported but not metabolized by the maltose-maltodextrine system of *E. coli*. Bacteria uptake experiments indicate that *E-coli* take up $^{14}$C-acarbose and $^{14}$C-maltose in a similar rate (Brunkhorst C, et all, J. Bact, April 1999, p 2012).

Embodiments of the present disclosure include methods for imaging a sample (e.g., tissue or cell(s)) or a subject (e.g., mammal), that includes contacting a sample with or administering to a subject a labeled probe (e.g., [18F]-fluoromaltose probe and [18F]-fluoroacarbose probe) and imaging with a PET imaging system. The imaging can be performed in vivo and/or in vitro. In particular, embodiments of the present disclosure can be used to image bacterial infection. In this regard, the sample or subject can be tested to determine if the sample or subject includes a bacterial infection, monitor the progression (or regression) of the bacterial infection, assess the response of the bacterial infection to treatment, and the like. In an embodiment, the tissue or cells can be within a subject or have been removed from a subject.

In an embodiment, the labeled probe (e.g., [18F]-fluoromaltose probe and [18F]-fluoroacarbose probe) can be imaged using imaging systems such as positron emission tomography (PET) imaging systems. In an embodiment, PET imaging is a preferred embodiment. Other types of labeled maltose probes can use appropriate imaging systems.

In an embodiment, the labeled probe can be used in diagnosing, localizing, monitoring, and/or assessing bacterial infections. In particular, the present disclosure includes methods relating to non-invasive imaging (e.g., using positron emission tomography (PET) imaging system) using the labeled maltose probe in vivo.

Embodiments of the present disclosure can be used to target bacteria, in particular, bacterial infections, in a subject such as a mammal, specifically, a human, since mammalian cells do not take up the labeled maltose probe and the pathogenic bacteria takes up the labeled maltose prove.

In an embodiment, the labeled probe can include a radiolabeled maltose probe or a radiolabeled acarbose probe. In an embodiment, the radiolabeled maltose probe or the radiolabeled acarbose probe can have one of the structures as shown in FIGS. 1A and 1B. RI is radioisotope and is also referred to as a radiolabel. In an embodiment, the radiolabel can include one of the following: $^{18}$F, $^{125}$I, $^{124}$I, $^{131}$I, $^{123}$I, $^{32}$Cl, $^{33}$Cl, $^{34}$Cl, $^{74}$Br, $^{75}$Br, $^{76}$Br, $^{77}$Br, or $^{78}$Br. In an embodiment, the radiolabel can be $^{18}$F. In an embodiment, the radiolabel can be positioned at the 1, 2, or 6 position of the D-glucopyranoside. In an embodiment, the labeled maltose probe can include: 1-$^{18}$F-maltose probe, 2-$^{18}$F-maltose probe, and 6-$^{18}$F-maltose probe. In an embodiment, the labeled acarbose probe can include: 1-$^{18}$F-acarbose probe, 2-$^{18}$F-acarbose probe and 6-$^{18}$F-acarbose probe. In an embodiment, the radiolabel can include $^{11}$C, which can be any one of the carbon atoms, for either the radiolabeled maltose probe or a radiolabeled acarbose probe.

In an embodiment, each of the 1-$^{18}$F-maltose probe, 2-$^{18}$F-maltose probe, 6-$^{18}$F-maltose probe, and the 1-$^{18}$F-acarbose probe, 2-$^{18}$F-acarbose probe and 6-$^{18}$F-acarbose probe, includes a label, $^{18}$F, that can be used to detect, image, or otherwise identify the probe, quantify the amount of the probe, determine the location of the probe (e.g., in imaging), and combinations thereof. As noted above, these labeled probes can be associated and/or correlated with a bacterial infection, thus the detection of the probe in a location can be used to identify the location of the bacterial infection. Additional details regarding the labeled maltose probe are described in Example 1.

Embodiments of the labeled maltose probes can be made using a synthesis as shown in FIGS. 2.1A-2.1C and described in Example 1. In an embodiment such as that shown in FIGS.

2.1A and 2.1B, the synthesis utilizes the reaction between the leaving group nosylate (e.g., other leaving groups can be used as well) and anhydrous [$^{18}$F]KF/Kryptofix 2.2.2 in acetonitrile (or other appropriate solvent such as dimethylsulfoxide, dimethylformamide, acetone, alcohols, benzene, toluene, tetrahydrofurane ethers and dioxanes) to produce 1,2,3-tri-O-acetyl-4-O-(2',3'-di-O-acetyl-4',6'-benzylidene-α-D-glucopyranosyl)-6-deoxy-6-[$^{18}$F]fluoro-D-glucopranoside. Then, the compound undergoes acid hydrolysis followed by its basic hydrolysis to produce the final 6-[$^{18}$F]-fluoromaltose compound. In another embodiment shown in FIG. 2.1C, the 1-[$^{18}$F]-labeled maltose derivative was prepared by nucleophilic displacement of triflate group (e.g., another group can be as well) in the precursor compound by [$^{18}$F]fluoride ion using anhydrous [$^{18}$F]KF/Kryptofix 2.2.2. The compound is then de-protected with basic hydrolysis to afford 4-O-(α-D-glucopyranosyl)-1-deoxy-1-[$^{18}$F]-fluoro-D-glucopyranoside (1-[$^{18}$F]fluoromaltose).

Embodiments of the labeled acarbose probes can be made using a synthesis as shown in FIGS. 3.1-3.2 and described in Example 2. In an embodiment as shown in FIGS. 3.1 and 3.2, the [$^{18}$F]-labeled acarbose derivative was prepared by nucleophilic displacement of nosylate group (e.g., another group can be used as well) by [$^{18}$F]fluoride ion using anhydrous [$^{18}$F]KF/Kryptofix 2.2.2. The compound is then de-protected with basic hydrolysis to afford [$^{18}$F]-6-fluoroacarbose.

In each synthesis, it should be noted that alternative protecting groups can be used to replace the acetyl group, the trityl group, and/or nosylate group so as long as any replacement(s) permit the synthesis to produce the desired labeled probe. For example, the acetyl group can be replaced with one of the following: benzoyl, benzyl, methoxymethyl, allyl, t-butyldimethylsilyl, tetrahydropyranyl, t-butyldiphenylsilyl and t-butyl; the trityl group can be replaced with one of the following: methoxyphenyldiphenylmethyl, t-butyldimethylsilyl, tetrahydropyranyl, t-butyldiphenylsilyl and t-butyl; and the nosylate group can be replaced with one of the following: tosylate, triflate, brosylate, mesylate, and thiolate groups.

It should be noted that portions of the present disclosure discuss labeled maltose probes and labeled acarbose probes while other portions describe a specific embodiment of the labeled maltose probes and labeled acarbose probes. Discussions focusing on the labeled maltose probes and labeled acarbose probes are not limiting to the scope of the disclosure, rather those discussions are merely describing an exemplary embodiment of the present disclosure.

Methods of Use

Embodiments of this disclosure include, but are not limited to: methods of imaging a sample or a subject using the labeled probe (e.g., [18F]-fluoromaltose probe or [18F]-fluroacarbose); methods of imaging a bacterial infection, using the labeled probe (e.g., [18F]-fluoromaltose probe or [18F]-fluroacarbose); methods of diagnosing a bacterial infection using the labeled probe (e.g., [18F]-fluoromaltose probe or [18F]-fluroacarbose); methods of monitoring the progress of a bacterial infection using the labeled probe (e.g., [18F]-fluoromaltose probe or [18F]-fluroacarbose), and the like.

Embodiments of the present disclosure can be used to image, detect, study, monitor, evaluate, assess, and/or screen, a bacterial infection in vivo or in vitro using the labeled probe (e.g., [18F]-fluoromaltose probe or [18F]-fluroacarbose). Although reference below is made to the use of the [18F]-fluoromaltose probe, other probes (e.g., [18F]-fluroacarbose) described herein can be used in the alternative.

In a particular embodiment, the [18F]-fluoromaltose probe can be used in imaging a bacterial infection. For example, the [18F]-fluoromaltose probe is provided or administered to a subject in an amount effective to result in uptake of the [18F]-fluoromaltose probe into the bacterial infection. The subject is then introduced to an appropriate imaging system (e.g., PET system) for a certain amount of time (e.g., this depends on radioisotope being used). The bacterial infection that takes up the [18F]-fluoromaltose probe could be detected using the imaging system. The location of the detected signal from the [18F]-fluoromaltose probe can be correlated with the location of bacterial infection. In an embodiment, the dimensions of the location can be determined as well. Other labeled maltose probes and labeled acarbose probes can be used in a similar manner.

In an embodiment, the steps of this method can be repeated at determined intervals so that the location and/or size of the bacterial infection can be monitored as a function of time and/or treatment. In particular, the [18F]-fluoromaltose probe can find use in a host undergoing treatment, to aid in visualizing the response of bacterial infection to the treatment. In this embodiment, the [18F]-fluoromaltose probe is typically visualized and sized prior to treatment, and periodically (e.g., hourly, daily, weekly, monthly, intervals in between these, and the like) during treatment, to monitor the bacterial infection. Other labeled maltose probes and labeled acarbose probes can be used in a similar manner.

Embodiments of the [18F]-fluoromaltose probe also find use as a screening tool in vitro to select compounds for use in treating bacterial infection. The bacterial infection could be easily monitored by incubating the cells with the bacterial infection with the [18F]-fluoromaltose probe during or after incubation with one or more candidate drugs. The ability of the drug compound to affect the disease can be imaged over time using the [18F]-fluoromaltose probe. Other labeled maltose probes and labeled acarbose probes can be used in a similar manner.

It should be noted that the amount effective to result in uptake of the labeled probe (e.g., [18F]-fluoromaltose probe or [18F]-fluroacarbose) into the cells or tissue of interest may depend upon a variety of factors, including for example, the age, body weight, general health, sex, and diet of the host; the time of administration; the route of administration; the rate of excretion of the specific probe employed; the duration of the treatment; the existence of other drugs used in combination or coincidental with the specific composition employed; and like factors well known in the medical arts.

Kits

The present disclosure also provides packaged compositions or pharmaceutical compositions comprising a pharmaceutically acceptable carrier and a labeled probe (e.g., [18F]-fluoromaltose probe or [18F]-fluroacarbose) of the disclosure. In certain embodiments, the packaged compositions or pharmaceutical composition includes the reaction precursors to be used to generate the labeled probe according to the present disclosure. Other packaged compositions or pharmaceutical compositions provided by the present disclosure further include material including at least one of: instructions for using the labeled probe to image a subject, or subject samples (e.g., cells or tissues), which can be used as an indicator of conditions including, but not limited to, bacterial infection.

Embodiments of this disclosure encompass kits that include, but are not limited to, the labeled probe (e.g., [18F]-fluoromaltose probe or [18F]-fluroacarbose) and directions (written instructions for their use). The components listed above can be tailored to the particular biological condition (bacterial infection) to be monitored as described herein. The kit can further include appropriate buffers and reagents known in the art for administering various combinations of the components listed above to the subject. The labeled probe and carrier may be provided in solution or in lyophilized form. When the labeled probe and carrier of the kit are in lyophilized form, the kit may optionally contain a sterile and physiologically acceptable reconstitution medium such as water, saline, buffered saline, and the like.

Dosage Forms

Embodiments of the present disclosure can be included in one or more of the dosage forms mentioned herein. Unit dosage forms of the pharmaceutical compositions (the "composition" includes at least the labeled probe (e.g., [18F]-fluoromaltose probe or [18F]-fluroacarbose probe) of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

Typical compositions and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Embodiments of the present disclosure include pharmaceutical compositions that include the labeled probe (e.g., [18F]-fluoromaltose probe or [18F]-fluroacarbose probe), pharmaceutically acceptable salts thereof, with other chemical components, such as physiologically acceptable carriers and excipients. One purpose of a pharmaceutical composition is to facilitate administration of labeled probe (e.g., [18F]-fluoromaltose probe or [18F]-fluroacarbose probe) to a subject (e.g., human).

Embodiments of the present disclosure may be salts and these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an embodiment of the present disclosure contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds may be formed, for example, by reacting an active compound with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

The amounts and a specific type of active ingredient (e.g., a labeled probe such as [18F]-fluoromaltose probe or a [18F]-fluroacarbose probe) in a dosage form may differ depending on various factors. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction

This Example describes the development of a novel positron emission tomography (PET) agent to visualize bacterial infections and monitor the therapeutic response to bacterial infections. We have developed a novel way to synthesize 4-O-(α-D-glucopyranosyl)-6-deoxy-6-[$^{18}$F]-fluoro-D-glucopyranoside (6-[$^{18}$F]-fluoromaltose) as a bacterial infection PET imaging agent. 6-[$^{18}$F]-fluoromaltose was prepared from precursor 1,2,3-tri-O-acetyl-4-O-(2',3',-di-O-acetyl-4',6'-benzylidene-α-D-glucopyranosyl)-6-deoxy-6-nosyl-D-glucopranoside (5). The synthesis utilizes the reaction between the leaving group nosylate in 5 and anhydrous [$^{18}$F]KF/Kryptofix 2.2.2 in acetonitrile at about 80° C. for about 10 minutes to produce 1,2,3-tri-O-acetyl-4-O-(2', 3'-di-O-acetyl-4',6'-benzylidene-α-D-glucopyranosyl)-6-deoxy-6-[$^{18}$F]fluoro-D-glucopyranoside (6). Finally, acid hydrolysis of 6 followed by its basic hydrolysis produced the final 6-[$^{18}$F]-fluoromaltose. A reliable synthesis of 6-[$^{18}$F]-fluoromaltose has been accomplished in 5-8% radiochemical (decay corrected with 95% chemical and radiochemical purities). Bacteria uptake experiments indicate that *E-coli* take up 6-[$^{18}$F]-fluoromaltose. Competition assays showed that the uptake of the 6-[$^{18}$F]-fluoromaltose was completely blocked by co-incubation with 1 mM of the natural substrate maltose. For the first time to the best of our knowledge, we have successfully synthesized 6-[$^{18}$F]-fluoromaltose via direct fluorination of an appropriate precursor of a protected maltose.

Introduction:

Although there are significant developments of microbiology of infection, infection still is in the rise throughout the world [1]. Due to poor diagnosis of bacterial infections and their ineffective antibiotics treatment of bacterial drug resistance, bacterial infections remain the major health issue. It is important to distinguish bacterial infection from nonbacterial inflammation [2]. Although imaging modalities such as computed tomography (CT) and magnetic resonance imaging (MRI) provide excellent structural images but they are unable to recognize bacterial infection from nonbacterial inflammation [3]. Modern imaging modalities such as single-photon emission computer tomography (SPECT) or positron emission tomography (PET) with proper radiotracers could be used to distinguish bacterial infection from nonbacterial inflammation. Furthermore, SPECT and PET can be used for early detection and monitoring the treatment of bacterial infections. The most promising of these was the study by Diaz et al [4] using positron emission tomography (PET) and [$^{124}$I]-1-(2'-deoxy-2'-fluoro-β-D-arabinofuranosyl)-5-iodouracil (FIAU), to identify bacterial lesions in patients with suspected musculoskeletal infections. The main limitation of this study is the fact that FIAU is a substrate of the bacterial enzyme-thymidine kinase but also the mammalian mitochondrial thymidine kinase and this leads to increased background in certain tissues. There have been several attempts to image bacterial infection in pre-clinical models using bioluminescent and fluorescent strains of bacteria. In a recent study Murthy N et al [5] have demonstrated the use of fluorescent maltodextrin-based probes to image bacteria in pre-clinical models with a high degree of specificity and sensitivity. Maltose and maltodextrins appear to be used as energy sources exclusively by bacteria [6]. Many species of bacteria including pathogenic strains express a series of genes (commonly known as the maltodextrin transport complex) that accomplish the binding, transport and utilization of maltose and maltodextrin. This transport mechanism is absent in mammalian cells [7] making maltose a substrate unique to bacteria and hence an ideal choice to build imaging probes directed against bacteria. Since PET is the most clinically relevant imaging modality, we would like to develop a novel maltose based PET agents to label and image bacteria in vitro and in vivo. The maltose based PET agents can be used to detect, monitor, evaluate, assess and/or screen a bacterial infection.

Although the syntheses of 1-fluoromaltose [8-11] and 6-fluoromaltose [8, 12-14] (FIG. 1.1) have been described but the preparation an $^{18}$F-labelled fluoromaltose has not been reported yet. Here, we report the synthesis of 4-O-(α-D-glucopyranosyl)-6-deoxy-6-[$^{18}$F]-fluoro-D-glucopyranoside (6-[$^{18}$F]-fluoromaltose, 7) and 4-O-(α-D-glucopyranosyl)-1-deoxy-1-[$^{18}$F]-fluoro-D-glucopyranoside (1-[$^{18}$F]-fluoromaltose, 11) as possible bacterial infection PET imaging agents.

Materials and Methods:

General:

Chemicals were purchased from Aldrich chemical company (Milwaukee, Wis.). 6-Floromaltose and 1-fluoromaltose were synthesized according to the literature procedure [8-14] (FIG. 1.1). 6-[$^{18}$F]-fluoromaltose was prepared from precursor 1,2,3-tri-O-acetyl-4-O-(2',3'-di-O-acetyl-4',6'-benzylidene-α-D-glucopyranosyl)-6-deoxy-6-nosyl-D-glucopranoside (5) (scheme 1 and 2). 6-[$^{18}$F]-fluoromaltose purification was performed on a Dionex HPLC system (Dionex Corporation, Sunnyvale, Calif.) equipped with a Dionex P680 quaternary gradient pump and Knauer K-2001 UV detector (Berlin Germany) set at 254 nm and radioactivity detector (Carroll & Ramsey Associates, model 1055, Berkeley, Calif.). Semi preparative HPLC reverse phase column (Phenomenex, Gemini, Hesperia, Calif., C18, 5μ, 10 mm×250 mm) with the mobile phase water/acetonitrile (99/1) and flow rate of 3 mL/min under isocratic condition was used for purification of 6-[$^{18}$F]-fluoromaltose. Radioactivity measurements were performed by A CRC-15R PET dose calibrator (Capintec Inc., Ramsey, N.J.) 400 MHz spectrometer. Analytical HPLC was carried out using Lab Alliance (LA, Stat College. PA) system equipped with a LA Series III HPLC pump (1 mL/min), LA Model 500 UV detector (254 nm), Carroll & Ramsey Associates (Berkley, Calif.), and an SRI Instrument Model 202 four-channel serial port chromatography data system using PEAK simple software (Torrance Calif.). Analytical HPLC reverse phase column (Phenomenex, Gemini, Hesperia, Calif., C18, 5μ, 4.6 mm×250 mm) with the mobile phase 2 mM ammonium formate, 0.1% HCOOH, PH 5.6/methanol (98/2) and flow rate of 1 mL/min under isocratic condition was used for analysis of 6-[$^{18}$F]-fluoromaltose.

No carrier-added [$^{18}$F]fluoride was prepared by the $^{18}$O(p, n)$^{18}$F nuclear reaction on a GE PET tracer cyclotron. [$^{18}$F] Fluoride processing and synthesis of crude 1,2,3-tri-O-acetyl-4-O-(2',3'-di-O-acetyl-4',6'-benzylidene-α-D-glucopyranosyl)-6-deoxy-6-[$^{18}$F]fluoro-D-glucopranoside (6) were completed in the GE TRACER lab FX-FN synthesis module (GE Medical System, Milwaukee, Wis.). The crude 6 were hydrolyzed by 1N HCl followed by 2N NaOH and injected into a C18 reverse phase semi-preparative HPLC column (Phenomenex Gemini, C18, 5μ, 10 mm×250 mm, flow rate of 3 mL/min, 2 mL loop). The mobile phase was and HPLC performed under isocratic condition. The product 6-[$^{18}$F]-fluoromaltose was collected at 6 min. in to a collection flask. After evaporation of solvent it was dissolved in saline and transferred into a sterile receiving vial through sterile Millipore GP-filter (0.2 μm). The chemical and radiochemical purities of 6-[$^{18}$F]-fluoromaltose was determined by reverse phase analytical HPLC method (Phenomenex Gemini C18, 5μ, 4.6×250 mm) and was more than 95% pure. The radio synthesis time was 120 min and the radiochemical yield was 5-8% (n=8, decay corrected).

1,2,3-tri-O-acetyl-4-O-(2',3'-di-O-acetyl-4',6'-benzylidene-α-D-glucopyranosyl)-6-deoxy-6-O-trityl-D-glucopranoside (3)

A solution of 4',6'-benzylidene-α-D-glucopyranosyl-D-glucopranoside [8, 12](2,187 mg, 0.43 mmol) in dry pyridine (1.5 mL) containing trityl chloride (184 mg, 0.66 mmol) was kept at room temperature for 7 h. After addition of acetic anhydride (1.5 ml) the reaction mixture was stirred in room temperature for 24 h. Finally the reaction mixture was evaporated under vacuum and the residue was co-evaporated with toluene. The crude product was purified by column chromatography (silica gel) using 70/30 ethyl acetate and hexane as the eluent to afford 91 mg (24%) of 4 as a foam with α/β=.0.7/1. α-anomer: $^1$H NMR (400 MHz, CDCl$_3$) δ ppm: 7.15-7.44 (m, 20H, H-phenyl), 6.33 (d, 1H, J=3.8 Hz, H-1), 5.49 (broad t, 1H, J=9.2 Hz, H-3), 5.39 (s, 1H, CH-phenyl), 5.21-5.29 (m, 4H, H-1', H-2, H-2' and H-3'), 4.99-5.05 (m, 1H, H-6'a), 4.79-4.80 (m, 1H, H-4), 3.98-4.07 (m, 1H, H-6a), 3.69-3.80 (m, 1H, H-5'), 3.54-3.62 (m, 2H, H-6b and H-5), 3.41-3.51 (m, 2H, H-6'b and H-4'), 2.20-2.21 (5s, 15H, CH3), α-anomer: $^1$H NMR (400 MHz, CDCl$_3$) δ ppm: 7.15-7.44 (m, 20H, H-phenyl), 5.75 (d, 1H, J=7.6 Hz, H-1), 5.39 (s, 1H, CH-phenyl), 5.21-5.29 (m, 5H, H-1', H-2, H-2', H-3 and H-3'), 4.99-5.05 (m, 1H, H-6'a), 4.79-4.80 (m, 1H, H-4), 3.98-4.07 (m, 1H, H-6a), 3.69-3.80 (m, 1H, H-5'), 3.54-3.62 (m, 1H, H-6b), 3.41-3.51 (m, 2H, H-6'b and H-4'), 3.24-3.31 (m, 1H, H-5), 2.00-2.21 (5s, 15H, CH3).

1,2,3-tri-O-acetyl-4-O-(2',3'-di-O-acetyl-4',6'-benzylidene-α-D-glucopyranosyl)-D-glucopranoside (4)

Compound 3 (76 mg, 0.086 mmol) in 2 mL of aqueous acetic acid (80% in water) was stirred for 75 minutes at 45° C. [15]. The mixture was concentrated under vacuum and the crude benzylidene 4 purified by column chromatography (silica gel) using 94/6 chloroform and methanol (90% in water) as the eluent to afford 34 mg (62%) of 4 as colorless viscous oil with α/β=1.1/1. α-anomer: $^1$H NMR (400 MHz, CDCl$_3$) δ ppm: 7.32-7.46 (m, 5H, H-phenyl), 6.25 (d, 1H, J=4.0 Hz, H-1), 5.56 (t, J=9.6 Hz, 1H, H-3), 5.50 (s, 1H, CH-phenyl), 5.44-5.52 (m, 1H, H-5'), 5.42 (d, J=4.4 Hz, 1H, H-1'), 5.33 (t, J=9.2 Hz, 1H, H-2), 4.84-5.00 (m, 3H, H-2', H-5 and H-6a'), 4.31-4.38 (m, 1H, H-6a), 4.2 (t, J=9.4 Hz, 1H, H-3'), 3.85-4.00 (m, 2H, H-4, H-6b), 3.69-3.77 (m, 1H, H-6'b), 3.60-3.68 (m, 1H, H-4'), 1.99-2.21 (5s, 15H, CH3), α-anomer: $^1$H NMR (400 MHz, CDCl$_3$) δ ppm: 7.32-7.46 (m, 5H, H-phenyl), 5.73 (d, 1H, J=8.4 Hz, H-1), 5.56 (t, J=9.6 Hz, 1H, H-3), 5.50 (s, 1H, CH-phenyl), 5.44-5.52 (m, 1H, H-5'), 5.42 (d, J=4.4 Hz, 1H, H-1'), 5.33 (t, J=9.2 Hz, 1H, H-2), 4.84-5.00 (m, 2H, H-2' and H-6a'), 4.31-4.38 (m, 1H, H-6a), 4.2 (t, J=9.4 Hz, 1H, H-3'), 3.85-4.00 (m, 3H, H-4, H-5, H-6b), 3.69-3.77 (m, 1H, H-6'b), 3.60-3.68 (m, 1H, H-4'), 1.99-2.21 (5s, 15H, CH3), MS: Calcd for [$C_{29}H_{36}O_{16}$]: 640.59: ESIMS found: [M+Na]$^+$ 663.59.

1,2,3-tri-O-acetyl-4-O-(2',3'-di-O-acetyl-4',6'-benzylidene-α-D-glucopyranosyl)-6-deoxy-6-O-nosyl-D-glucopranoside (5)

4-Nitrophenylsulfonyl chloride (98 mg, 0.442 mmol) in was added to a solution of 4 (54, 0.084 mmol) in CH$_2$Cl$_2$ (1.0 mL) containing triethylamine (84 μl) [16]. The mixture was stirred for 70 min at 0-5° C. and concentrated under vacuum. The crude nosylate 5 was purified by column chromatography (silica gel) using 1/1 ethyl acetate and hexane as the eluent to afford 50 mg (72%) of 5 as colorless viscous oil with α/β=1.1/1. α-anomer: $^1$H NMR (400 MHz, CDCl$_3$) δ ppm: 8.24 (d, J=9.2 Hz, 2H, H-nitrophenyl), 8.10 (d, J=9.00 Hz, 2H, H-nitrophenyl), 7.36-7.48 (m, 5H, H-phenyl), 6.03 (d, 1H, J=3.7 Hz, H-1), 5.52 (s, 1H, CH-phenyl), 5.42-5.49 (m, 1H, H-3), 5.33-5.42 (m, 2H, H-1' and H-3'), 5.22 (t, J=9.2 Hz, 1H, H-2), 4.87 (dd, J=10 Hz, J=4.1 Hz, 1H, H-2'), 4.86 (dd, J=9.6 Hz, J=4.2 Hz, 1H, H-6a'), 4.77 (t, J=9.0 Hz, 1H, H-4), 4.68 (dd, J=10 Hz, J=3.8 Hz, 1H, H-6a), 4.38-4.49 (m, 2H, H-5' and H-5), 4.00-4.08 (m, 1H, H6b), 3.69-3.80 (m, 2H, H-4' and H-6'b), 1.96-2.17 (5s, 15H, CH3), α-anomer: $^1$H NMR (400 MHz, CDCl$_3$) δ ppm: 8.20 (d, J=9.0 Hz, 2H, H-nitrophenyl), 8.10 (d, J=9.00 Hz, 2H, H-nitrophenyl), 7.36-7.48 (m, 5H, H-phenyl), 5.63 (d, 1H, J=8.1 Hz, H-1), 5.52 (s, 1H, CH-phenyl), 5.33-5.42 (m, 2H, H-1' and H-3'), 5.22 (t, J=9.2 Hz, 1H, H-2), 4.87 (dd, J=10 Hz, J=4.1 Hz, 1H, H-2'), 4.86 (dd, J=9.6 Hz, J=4.2 Hz, 1H, H-6a'), 4.77 (t, J=9.0

Hz, 1H, H-4), 4.68 (dd, J=10 Hz, J=3.8 Hz, 1H, H-6a), 4.38-4.49 (m, 2H, H-3, H-5'), 4.00-4.08 (m, 1H, H6b), 3.69-3.80 (m, 2H, H-4' and H-6'b), 3.61-3.68 (m, 1H, H-5), 1.96-2.17 (5s, 15H, CH3). MS: Calcd for [$C_{35}H_{39}O_{20}NS$]: 825.74: ESIMS found: [M+Na]$^+$ 847.84.

4-O-(α-D-glucopyranosyl)-6-deoxy-6-[$^{18}$F]-fluoro-D-glucopyranoside(6-[$^{18}$F]-fluoromaltose, 7)

No carrier-added [$^{18}$F]fluoride trapped on a QMA cartridge was elated with a solution of $K_2CO_3$ (3.5 mg) and kryptofix 2.2.2 (15 mg) in water (0.1 mL) and acetonitrile (0.9 mL). The solvent was removed under vacuum at about 65° C. and to the anhydrous residue was added a solution of nosylate precursor 5 (4-5 mg) in acetonitrile (0.8 mL). The mixture was heated for about 10 min at about 80° C. After cooling to room temperature, 10 mL of water was added and the solution passed through a light C-18 Sep-pack cartridge (Water) and the crude protected 6-[$^{18}$F]-fluoromaltose (6) removed by passing 3 mL of acetonitrile trough the cartridge. The crude 6 was concentrated and hydrolyzed first by 1N HCl at about 110° C. for about 10 min then by 2N NaOH in room temperature for 4 min to afford crude 6-[$^{18}$F]-fluoromaltose 7. The neutral solution of 7 was injected into a C18 reverse phase semipreparative HPLC column (Phenomenex Gemini, C-18, 5μ, 10 mm×250 mm), flow rate of 3 mL/min and 2 mL loop. The mobile phase was 1% acetonitrile in water and HPLC performed under isocratic condition. The product 6-[$^{18}$F]-fluoromaltose (7) was collected at 6 min. in to a collection flask. After evaporation of solvent it was dissolved in saline and transferred into a sterile receiving vial through sterile Millipore GP-filter (0.2 μm). The chemical and radiochemical purities of 6-[$^{18}$F]-fluoromaltose was determined by reverse phase analytical HPLC method (Phenomenex Gemini C18, 5μ, 4.6×250 mm) and was more than 95% pure. Also, radio TLC, of [$^{18}$F] 7 (silica gel plate, $CH_3CN/H_2O$; 70/30) gave an Rf value of 0.5 which is identical to the Rf value of 6-fluoromaltose [8] under the same TLC condition. The radio synthesis time was 120 min and the radiochemical yield was 5-8% (decay corrected).

2,3,6-tri-O-acetyl-4-O-(2',3',4',6'-tetra-O-acetyl-α-D-glucopyranosyl)-1-deoxy-1-O-trifyl-D-glucopranoside (9)

Trifuorometanesulfonic anhydride (12 μl, 0.071 mmol) was added into a solution of 8 [8-9](40 mg, 0.063 mmol) in $CH_2Cl_2$ (0.17 mL) containing pyridine (12 μl, 0.148 mmol) at 0-5° C. The mixture was stirred for 3 h at room temperature and diluted with 1.5 mL of $CH_2CL_2$. The $CH_2Cl_2$ solution, successively washed with cold saturated $NaHCO_3$ (1.5 mL), cold water (1.5 mL). The organic layer was dried ($Na_2SO_4$), concentrated under vacuum and the crude triflate 9 was purified by column chromatography (silica gel) using 1/1 ethyl acetate and hexane as the eluent to afford 14.5 mg (30%) of 9 as colorless foam with α/β=1/3. α-anomer: $^1$H NMR (400 MHz, $CDCl_3$) δ ppm: 6.40 (d, 1H, J=3.8 Hz, H-1), 5.68 (dd, J=9.6 Hz, J=8.6 Hz, 1H, H-3), 5.44 (d, 1H, J=4.1 Hz, H-1'), 5.32-5.39 (m, 1H, H-3'), 4.97 (dd, J=9.2 Hz, J=8.2 Hz, 1H, H-4'), 4.86-4.90 (m, 1H, H-2'), 4.78 (dd, 1H, J=9.8 Hz, J=3.7 Hz, 1H, H-2), 4.45 (dd, J=12.4 Hz, J=2.3 Hz, 1H, H-6a), 4.19-4.26 (m, 3H, H-5, H-6'a and H-6b), 4.00-4.10 (m, 1H, H4), 3.90-3.95 (m, 1H, H-6'b), 3.80-3.86 (m, 1H, H5'), 2.00-2.26 (7s, 21H, $CH_3$) $^{19}$F NMR ($CDCl_3$) δ ppm: −75.1 (s). α-anomer: $^1$H NMR (400 MHz, $CDCl_3$) δ ppm: 5.74 (d, J=8.2 Hz, 1H, H1), 5.41 (d, J=4.1 Hz, 1H, H1'), 5.35 (t, J=9.9 Hz, 1H, H3), 5.29 (t, J=9.0 Hz, 1H, H-3'), 5.06 (t, J=10 Hz, 1H, H-4'), 4.86 (dd, J=10.5 Hz, J=4.1 Hz, 1H, H-2'), 4.78 (dd, 1H, J=9.8 Hz, J=3.7 Hz, 1H, H-2), 4.45 (dd, J=12.4 Hz, J=2.3 Hz, 1H, H-6a), 4.19-4.26 (m, 3H, H-5, H-6'a and H-6b), 4.00-4.10 (m, 1H, H4), 3.90-3.95 (m, 1H, H-6'b), 3.80-3.86 (m, 1H, H5'), 2.00-2.26 (7s, 21H, CH3), $^{19}$F NMR ($CDCl_3$) δ ppm: −75.1 (s). MS: Calcd for [$C_{27}H_{35}O_{20}SF_3$]: 768.64: ESIMS found: [M+Na]$^+$ 791.1.

4-O-(α-D-glucopyranosyl)-1-deoxy-1-[$^{18}$F]-fluoro-D-glucopyranoside(1-[$^{18}$F]-fluoromaltose, 11)

No carrier-added [$^{18}$F]fluoride trapped on a QMA cartridge was eluted with a solution of $K_2CO_3$ (3.5 mg) and kryptofix 2.2.2 (15 mg) in water (0.1 mL) and acetonitrile (0.9 mL). The solvent was removed under vacuum at about 65° C. and to the anhydrous residue was added a solution of triflate precursor 9 (4-5 mg) in acetonitrile (0.8 mL). The mixture was heated for about 10 min at about 80° C. After cooling to room temperature, 10 mL of water was added and the solution passed through a light C-18 Sep-pack cartridge (Water) and the crude protected 1-[$^{18}$F]-fluoromaltose (10) removed by passing 3 mL of acetonitrile trough the cartridge. The crude 10 was concentrated and hydrolyzed by 0.5 mL of 2N NaOH in room temperature for about 4 min to afford crude 1-[$^{18}$F]-fluoromaltose 11. After addition of 1 mL of 1N HCl, the neutral solution of 11 was injected into a C18 reverse phase semipreparative HPLC column (Phenomenex Gemini, C-18, 5μ, 10 mm×250 mm), flow rate of 4 mL/min and 5 mL loop. The mobile phase was 1% acetonitrile in water and HPLC performed under isocratic condition. The product 1-[$^{18}$F]-fluoromaltose (11) was collected at 7 min. in to a collection flask. After evaporation of solvent it was dissolved in saline and transferred into a sterile receiving vial through sterile Millipore GP-filter (0.2 μm). The chemical and radiochemical purities of 1-[$^{18}$F]-fluoromaltose was determined by reverse phase analytical HPLC method (Phenomenex Gemini C18, 5μ, 4.6×250 mm) and was more than 95% pure. Also, radio TLC, of [$^{18}$F] 11 (silica gel plate, $CH_3CN/H_2O$; 70/30) gave an Rf value identical to the Rf value of 1-fluoromaltose [8] under the same TLC condition. The radio synthesis time was 110 min and the radiochemical yield was 4-6% (decay corrected).

Stability of 6-[$^{18}$F]Fluoromaltose in Serum

Serum (human or mouse) was centrifuged at about 4° C., maximum speed for about 10 min. About 330 μL of supernatant was transferred to an Eppendorf vial containing 20 μL of formulated radiolabelled 6-[$^{18}$F]fluoromaltose (50-100 μCi minimum). For control, same volume of radiolabelled compound in 330 μl PBS was used. After vortexing the radiolabelled mixtures, 70 μL aliquots transferred to Eppendorf tubes and incubated at about 37° C. At predetermine time points (e.g., 0, 5, 15, 30, 60 min) 140 μL of ice-cold methanol were added to corresponding samples to stop metabolism. After vortexing and centrifuging samples (10 min max speed), the supernatants were transferred to HPLC vials for HPLC analysis.

In Vitro Uptake Assays

A strain of E-.Coli (ATCC33456) and a mammalian cell line (EL4) were exposed to 1-[$^{18}$F]-fluoromaltose or [$^{18}$F]-6-fluoromaltose. All bacteria and cells were then washed in 1×PBS, lysed and radioactivity of each well was determined by gamma counter for $^{18}$F samples. All results were done in triplicate and are expressed in counts per minute (CPM), standard errors were determined and t tests performed. The uptake in E. Coli could also be blocked by co-incubation with 1 mM of cold maltose or 1 mM of 1-fluoromaltose.

Results:
Chemistry

Scheme 1 shows the synthesis of 1,2,3-tri-O-acetyl-4-O-(2',3'-di-O-acetyl-4',6'-benzylidene-α-D-glucopyranosyl)-6-deoxy-6-O-nosyl-D-glucopranoside (5), the [$^{18}$F]-6-fluoromaltose precursor. Treatment of benzylidene 2 [8] with trityl chloride followed by acetylation produced 1,2,3-tri-O-acetyl-4-O-(2',3'-di-O-acetyl-4',6'-benzylidene-α-D-glucopyranosyl)-6-deoxy-6-O-trityl-D-glucopranoside (3) in 24% yield. Selective deprotection of 3 resulted 4 in 62% which was nosylated [16] at ° C. to afford 5 in 72%. Scheme 3 shows the synthesis of 2,3,6-tri-O-acetyl-4-O-(2',3',4',6-tetra-O-acetyl-α-D-glucopyranosyl)-1-deoxy-1-O-trifyl-D-glucopranoside (9), the [$^{18}$F]-1-fluoromaltose precursor. Treatment of heptaperacetyl-1-hydroxymaltose 8 [8] with trifluoromethanesulfonic anhydride produced 9 in 30%.

Radiochemistry

[$^{18}$F]-labeled maltose derivative 6 (Scheme 2) was prepared by nucleophilic displacement of nosylate group in 5 by [$^{18}$F]fluoride ion in acetonitrile at about 80° C. for about 10 min. Initial purification of [$^{18}$F] 6 was performed via a light C-18 Sep-pack cartridge. After passing a solution of [$^{18}$F] 6 in acetonitrile through a light neutral alumina Sep-pack, it was smoothly hydrolyzed first by acid (1N HCl) at about 110° C. for about 10 min and then by base (2N NaOH) at room temperature for 4 min to yield [$^{18}$F]-6-fluoromaltose 7. The radiochemical yield was 5-8% (decay corrected, n=10). Likewise, 1-[$^{18}$F]-labeled maltose derivative 10 (Scheme 3) was prepared by nucleophilic displacement of triflate group in precursor 9 by [$^{18}$F]fluoride ion in acetonitrile at about 80° C. for about 10 min. [$^{18}$F]10 was purified by C-18 Sep-pack and de-protected with 2N NaOH to afford 4-O-(α-D-glucopyranosyl)-1-deoxy-1-[$^{18}$F]-fluoro-D-glucopyranoside (1-[$^{18}$F]fluoromaltose, 11). However, only α-anomer was stable under purification conditions.

Stability of 6-[$^{18}$F]Fluoromaltose in Serum

The percentage of intact 6-[$^{18}$F]fluoromaltose in PBS, human and mouse serum at 37° C. was determined by HPLC. FIG. 2.2 shows that percentage intact 6-[$^{18}$F]fluoromaltose at 2 h was lower than observed in 1 h (~96% at 1 h and ~65% in 2 h).

In Vitro Uptake Assays

To evaluate the ability of bacteria and cells to uptake [$^{18}$F]-6-fluoromaltose (7) and 1-[$^{18}$F]-fluoromaltose (11), a strain of E. Coli and a mammalian cell line (EL4) were exposed to 7 and 11. FIG. 2.3 shows the uptake of [$^{18}$F]-6-fluoromaltose by E. Coli and a mammalian cell line (EL4) indicates that [$^{18}$F]-6-fluoromaltose uptake is time dependent, unlike in E14 cells, where its uptake was minimal at 60 minutes post incubation with tracer. The uptake in E. Coli could also be blocked by co-incubation with 1 mM of cold maltose (98% blocking, p<0.0003), the natural substrate of the transporter. Likewise, $^3$H-maltose uptake in E. Coli was blocked both with 1 mM maltose and 1-fluoromaltose (FIG. 2.4).

Discussion:

We have developed a novel way to synthesize 4-O-(α-D-glucopyranosyl)-6-deoxy-6-[$^{18}$F]-fluoro-D-glucopyranoside (6-[$^{18}$F]-fluoromaltose, [$^{18}$F] 7) as a bacterial infection PET imaging agent. 6-[$^{18}$F]-fluoromaltose was prepared from precursor 1,2,3-tri-O-acetyl-4-O-(2',3'-di-O-acetyl-4',6'-benzylidene-α-D-glucopyranosyl)-6-deoxy-6-nosyl-D-glucopranoside (5). Scheme 1 describes the synthesis of 5. Compound 5 was characterized by $^1$H NMR and mass spectrometry (ESI-MS). The NMR spectrum showed new sets of doublets peak in the aromatic rejoin with an integration of 2H each and MS showed mass peak of 848.6 (M+Na). To the best of our knowledge, for the first time we have synthesized 4-O-(α-D-glucopyranosyl)-6-deoxy-6-[$^{18}$F]-fluoro-D-glucopyranoside ([$^{18}$F] 7, scheme 2) via a direct fluorination of 5 with anhydrous [$^{18}$F]KF/Kryptofix 2.2.2 in acetonitrile in 5-8% radiochemical yield (decay corrected) with 95% chemical and radiochemical purities.

In order to determine the stability of [$^{18}$F] 7 in human and mouse serum, [$^{18}$F] 7 was incubated in PBS (control), human and mouse serum at 37° C. up to 2 h. FIG. 2.2 shows that percentage intact 6-[$^{18}$F] 7 at 2 h was lower than observed in 1 h (~96% at 1 h and ~65% at 2 h). This could be due to defluorination of 6-[$^{18}$F] 7 at 2 h.

To test the ability of bacteria and cells to uptake [$^{18}$F]-6-fluoromaltose, a strain of E. Coli and a mammalian cell line (EL4) were exposed to [$^{18}$F] 7. FIG. 2.3 shows the uptake of [$^{18}$F] 7 by E. Coli and a mammalian cell line (EL4) indicates that [$^{18}$F]-6-fluoromaltose uptake is time dependent, unlike in E14 cells, where its uptake was minimal at 60 minutes post incubation with tracer. The uptake in E. Coli could also be blocked by co-incubation with 1 mM of cold maltose (98% blocking, p<0.0003), the natural substrate of the transporter. The rapid uptake is necessary if, with an isotope half-life of 110 minutes, is eventually going to prove efficacious as a PET tracer. Also, we tested 1-fluoromaltose in a competition assay as shown in FIG. 2.4. Here we allowed bacteria to take up $^3$H-labeled maltose for 10 mins. In a second set of bacterial samples we co-incubated the $^3$H-labeled radioactive maltose with 1 mM maltose which completely blocked the uptake of the radiolabeled maltose. In a third set of samples we co-incubated the $^3$H-labeled maltose with 1-fluoromaltose, which also completely blocked the uptake of the $^3$H-labeled maltose similar to the natural maltose. This experiment suggested that 1-fluoromaltose was being recognized and transported by the bacteria in a manner identical to maltose itself. However, later we found that 1-[$^{18}$F]fluoromaltose is not stable in vivo and very fast de-fluorinated which resulted a very high uptake of [$^{18}$F]fluoride ion by the bones.

References, each of which is incorporated herein by reference for the particular or relevant aspects:

1. Palestro C J (2009) Radionuclides imaging of infection: in search of the grail. J Nucl Med 50: 671-3.
2. Corstens F H M, van der Meer J W M (1999) Nuclear medicine's role in infection and inflammation. Lancet 354: 765-70.
3. Rakesh K, Sandip B, Drew T, Vivek A, Hongming Z, Abass A (2008). Role of modern imaging techniques for diagnoses of infection in the area of $^{18}$F-fluordeoxyglucose positron emission tomography. Clin Microbiol Rev 21: 209-24.
4. Diaz L A, Foss C A, Thornton K, Nimmagaddas S, Endress C J, Uzuner O, et al (2007) Imaging of Musculoskeletal Bacterial Infection by [$^{124}$I]FIAU-PET/CT PLoS ONE, 2(10):p. 21007.
5. Ning X, Lee S, Wang Z, Kim, D, Stubblefield B, Gilbert E, Murthy N (2011) Maltodextrine-based imaging probes detect bacteria in vivo with high sensitivity and specificity Nat Mater 10(8):602-7.
6. Dahl, M K, Manson M D (1985) interspecific reconstitution of maltose transport and chemotaxis in *Escherichia coli* with maltose binding protein from various enteric bacteria. J Bactriol 164: 1037-63.
7. Copal S, et al (2010) Maltose and maltodextrine utilization by *listeria monocytogenes* depend on an inducible ABC transporter which is repressed by glucose. PLoS ONE, 5:e 10349.
8. Braitsch M, Kahlig H, Kontaxis G, Fischer M, Kawada T, Knorat R, Schimd, W (2012) Synthesis of fluorinated maltose derivatives for monitoring protein interaction by 19F NMR. Beilstein J Org Chem, 8: 448-55.
9. Excoffier G, Gagnaire D, Utille J-P (1975) Coupure selective par l'hydrozine des groupments acetyles anomeres de residus glycosyles acetyls. Carbohydr Res, 39: 368-373
10. Toshima K (2000) Glycosyl fluorides in glycosidations. Carbohydr Res, 327: 15-26.
11. Lal G S, Pez G P, Pasaresi R J, Prozonic F M, Cheng S (1999) Bis(2-methyl)aminosulfur Trifluoride: A new Broad Spectrum Deoxofluorinating Agent With Enhanced Thermal Stability. J Org Chem, 64: 7048-7054.
12. Takeo K, Shinmitsu K (1984) A convenient synthesis of 6'-C-substituted b-maltose heptaacetates and of panose. Carbohydr Res, 133: 135-145.
13. Ye S, Rezende M M, Deng W-P, Herbert B, Daly J W, Johnson R A, Kirk K L (2004) Synthesis of 2',5'-Dideoxy-2-fluoroadenosine and 2',5'-Dideoxy-2,5'-difluoroadenosine: Potent P-Site Inhibitors of Adenylyl cyclase. J Med Chem, 47: 1207-1213.
14. Best W M, Stick R V, Tilbrook D M G (1997) The Synthesis of Some Epoxyalkyl-Deoxyhalo-b-cellobiosides. Aust J Chem, 50:13-18.
15. Dutton G G S, Slessor K N (1966) Synthesis of 6'-Substituted Maltose. Cana J Chem, 44:1069.
16. De Castro K A, Rhee H (2008) Selective Nosylation of 1-Phenylpropane-1,3-diol and Perchloric Acid Mediated Friedel-Crafts Alkylation: Key Steps for the New and Straightforward Synthesis of Toletero dine. Synthesis No. 12 P: 1841-1844.

Example 2

Synthesis of 6-[$^{18}$F]-Fluoroacarbose as a PET Tracer for Imaging Bacterial Infection Acarbose is a pseudooligosaccharide which is transported but not metabolized by the maltose-maltodextrine system of *Escherichia Coli* (Brunkhorst C, et all, J. Bact, April 1999, p 2012). $^{18}$F-Labeled acarbose would offer a good PET tracer for imaging bacterial infection.
Chemistry:
Scheme 1 (FIG. 3.1) shows the synthesis of dodecaacetyly-6-deoxy-6-O-nosyl-acarbose (4), the [$^{18}$F]-6-fluoroacarbose precursor. Treatment of acarbose (1) with trityl chloride followed by acetylation produced dodecaacetyl-6-deoxy-6-O-trityl-acarbose (2), in 29% yield. Selective deprotection of 2 resulted 3 in 62% which was nosylated at ° C. to afford 4 in 62% as the [$^{18}$F]-6-fluoroacarbose precursor. Compound 4 was characterized by $^1$H NMR and mass spectrometry (ESI-MS). The NMR spectrum showed new sets of doublets peak in the aromatic rejoin with an integration of 2H each and MS showed mass peak of 1336.2 (M+1).
Radiochemistry:
We have developed a novel way to synthesize [$^{18}$F]-6-fluoroacarbose 6 as a bacterial infection PET imaging agent. [$^{18}$F]-labeled acarbose derivative 5 (Scheme 2, (FIG. 3.2)) was prepared by nucleophilic displacement of nosylate group in 4 by [$^{18}$F]fluoride ion in acetonitrile at 80° C. for 10 min. Initial purification of [$^{18}$F]5 was performed via a light C-18 Sep-pack cartridge. After passing a solution of [$^{18}$F]5 in acetonitrile through a light neutral alumina Sep-pack, it was evaporated to dryness and smoothly hydrolyzed by base (0.5 M NaOCH$_3$ in methanol) at 80° C. for 5 min to yield [$^{18}$F]-6-fluoroacarbose 6 in 4-6% radiochemical yield (decay corrected).
It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim at least the following:
1. A method of imaging a bacterial infection in a subject comprising the following steps:
administering to the subject a labeled probe selected from the group consisting of:

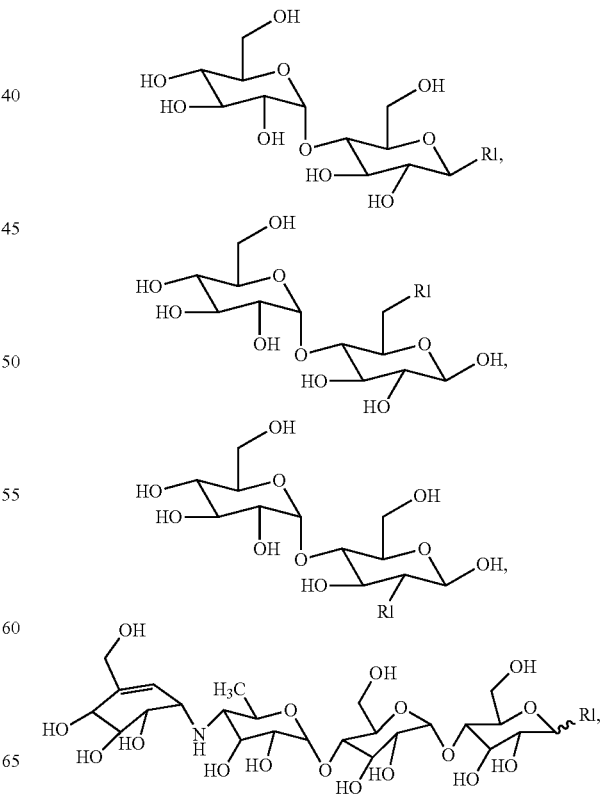

-continued

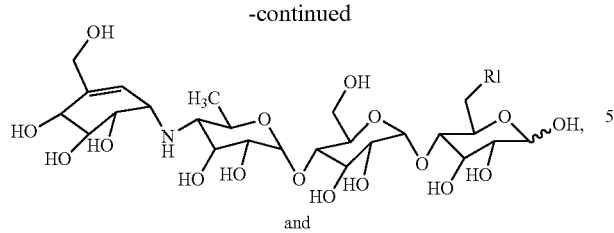

and

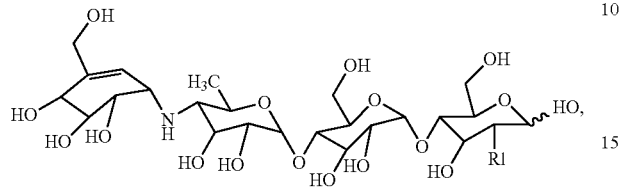

wherein R1 is a radiolabel, wherein the radiolabel is selected from the group consisting of: $^{18}$F, $^{125}$I, $^{124}$I, $^{131}$I, $^{123}$I, $^{32}$Cl, $^{33}$Cl, $^{34}$Cl, $^{74}$Br, $^{75}$Br, $^{76}$Br, $^{77}$Br, and $^{78}$Br;

imaging at least a portion of the subject; and detecting the labeled probe, wherein the location of the labeled probe corresponds to bacterial infection.

2. The method of claim 1, wherein the labeled probe has one of the following structures:

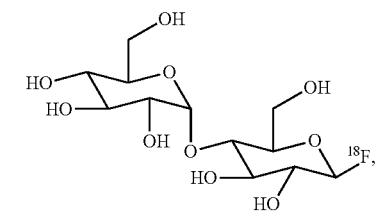

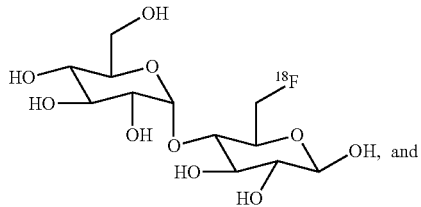

-continued

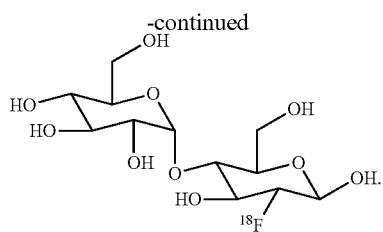

3. The method of claim 1, wherein the labeled probe is selected from the group consisting of:

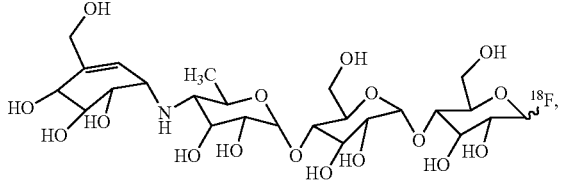

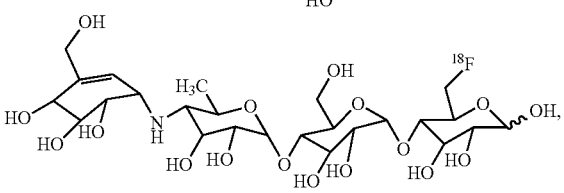

and

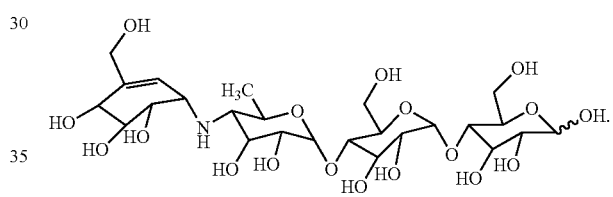

4. The method of claim 1, further comprising repeating the steps of claim 1 periodically to monitor the progress of a bacterial infection in the subject.

5. The method of claim 4, wherein monitoring includes monitoring the dimensions of the location corresponding to the bacterial infection.

* * * * *